US00PP30800P3

(12) United States Plant Patent
Hancock

(10) Patent No.: US PP30,800 P3
(45) Date of Patent: Aug. 13, 2019

(54) ***LEPIDOSPERMA* PLANT NAMED 'LEP01'**

(50) Latin Name: *Lepidosperma gladiatum*
Varietal Denomination: LEP01

(71) Applicant: David John Hancock, Whiteman (AU)

(72) Inventor: David John Hancock, Whiteman (AU)

( * ) Notice: Subject to any disclaimer, the term of this patent is extended or adjusted under 35 U.S.C. 154(b) by 6 days.

(21) Appl. No.: 15/731,733

(22) Filed: Jul. 25, 2017

(65) Prior Publication Data

US 2018/0027720 P1 Jan. 25, 2018

(30) Foreign Application Priority Data

Jul. 25, 2016 (AU) ..... PBR 2016/204

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373
CPC ..... A01H 5/12
See application file for complete search history.

*Primary Examiner* — Keith O. Robinson
(74) *Attorney, Agent, or Firm* — Samuel R. McCoy, Jr.

(57) ABSTRACT

'LEP01' is a distinctive cultivar of *Lepidosperma gladiatum* which is characterized by a short plant height, dense foliage and fine-texture foliage. The new variety propagates successfully by division and tissue culture and has shown to be uniform and stable in the resulting generations from asexual propagation.

2 Drawing Sheets

Latin name of the genus and species: The Latin name of the genus and species of the novel variety disclosed herein is *Lepidosperma gladiatum.*

Variety denomination: The inventive variety of *Lepidosperma gladiatum* disclosed herein has been given the variety denomination 'LEP01'.

CROSS REFERENCE TO RELATED APPLICATIONS

This application claims priority to the Australian Plant Breeders Rights application number 2016/204, filed on Jul. 25, 2016, which is herein incorporated by reference.

BACKGROUND OF THE INVENTION

Parentage: 'LEP01' is a seedling selection resulting from a selection process carried out by the inventor in Joondalup, Western Australia, Australia. In August of 2010, the inventor sowed seed collected from several unnamed *Lepidosperma gladiatum* plants and grew them to a mature size in order to evaluate for unique characteristics of commercial value. In March of 2011, the inventor discovered a seedling of *Lepidosperma gladiatum* which exhibited a smaller plant size and fine-textured foliage. This seedling was isolated and further evaluated to assess the uniformity and stability of the characteristics first observed. After 3 years of propagation trials, the claimed plant was selected for commercial production and given the name 'LEP01'.

Asexual Reproduction: 'LEP01' was first asexually propagated in 2011 by division of the plant's crown in Joondalup, Western Australia, Australia and has since been asexually reproduced by meristematic tissue culture propagation. The distinctive characteristics of the inventive 'LEP01' variety have proven to be stable through five generations and clones so produced maintain the distinguishing characteristics of the original plant.

SUMMARY OF THE INVENTION

'LEP01' is a distinctive cultivar of *Lepidosperma gladiatum* which is characterized by a short plant height, dense foliage and fine foliage texture.

BOTANICAL DESCRIPTION OF THE PLANT

Figure 1:
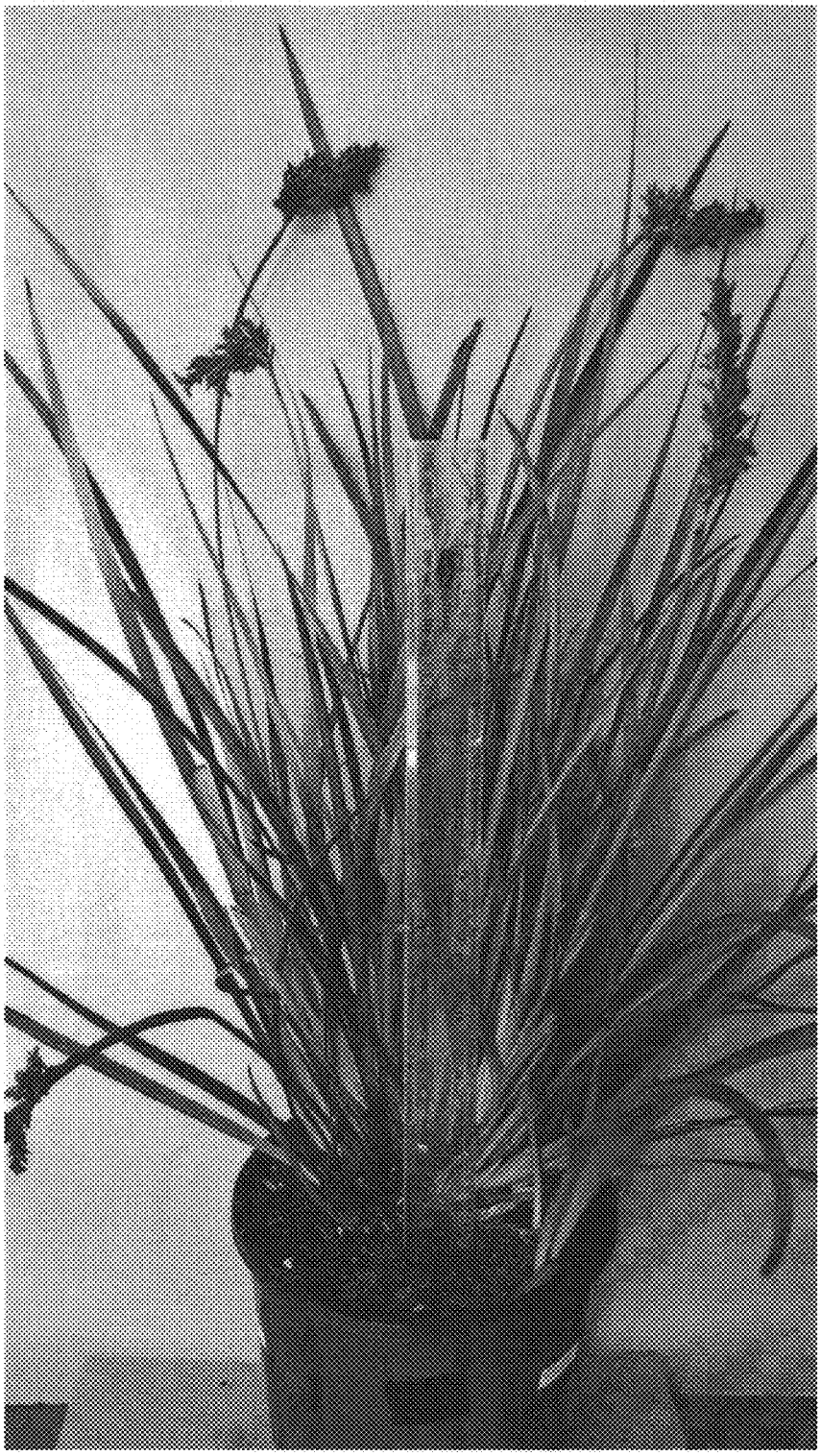
FIG. 1 illustrates, as true as is reasonably possible to obtain in color photographs of this type, an exemplary 'LEP01' specimen of approximately 12 months of age in a 250 mm nursery pot, grown at a commercial plant breeding facility in Clarendon, NSW, Australia.
Figure 2:
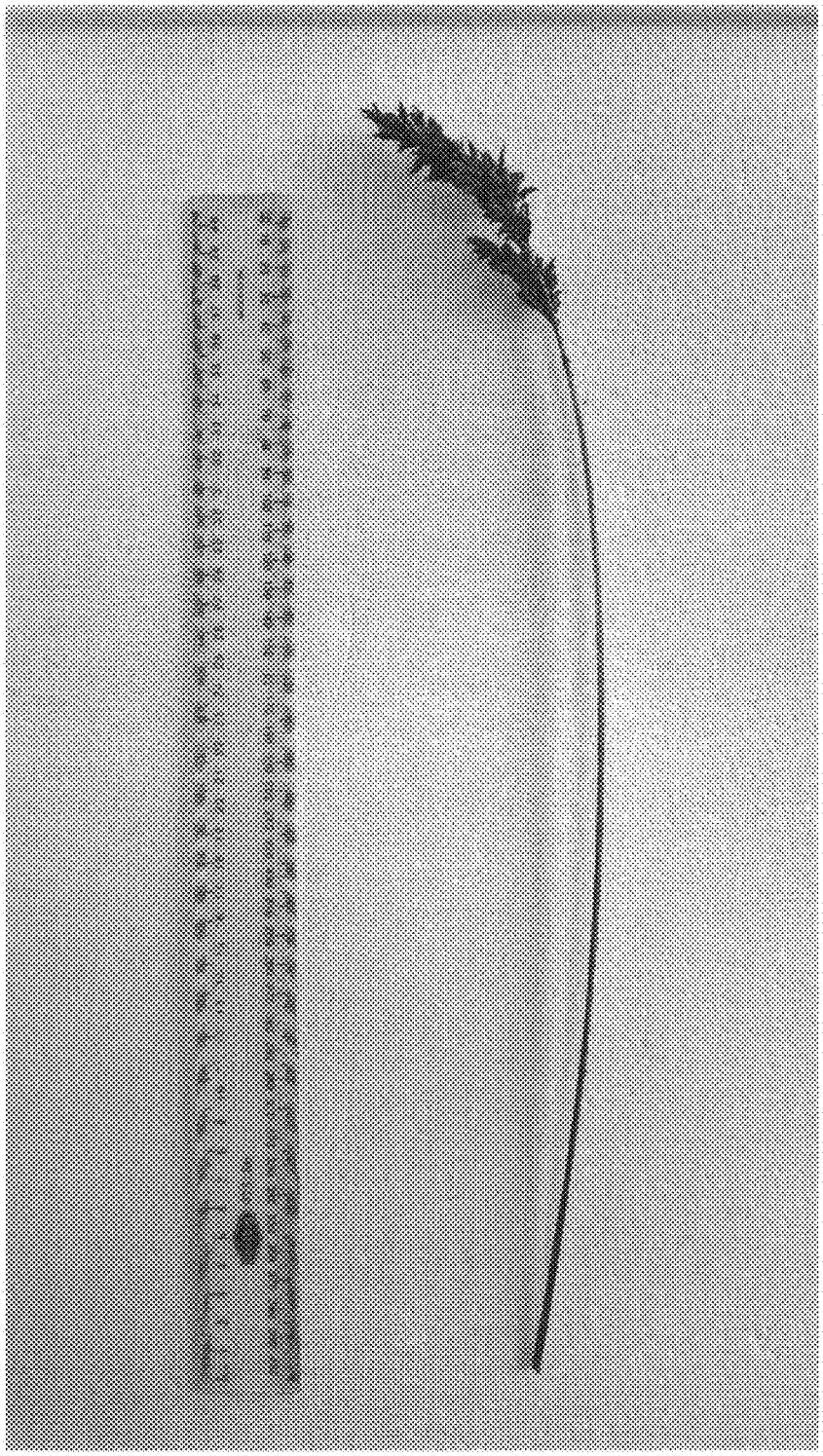
FIG. 2 illustrates, as true as is reasonably possible to obtain in color photographs of this type, an exemplary inflorescence of 'LEP01'.

The following is a detailed botanical description of a new and distinct variety of a *Lepidosperma* ornamental plant known as 'LEP01'. Plant observations were made on plants grown in Clarendon, NSW, Australia. Unless indicated otherwise, the descriptions disclosed herein are based upon observations made in June of 2017 of three year-old 'LEP01' plants grown outdoors from rooted cuttings in 200 mm nursery pots filled with soilless potting media, maintained with granular slow release fertilizer and regularly watered with overhead irrigation. No pest and disease measures were taken.

Those skilled in the art will appreciate that certain characteristics will vary with older or, conversely, younger plants. 'LEP01' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2001 edition.

A botanical description of 'LEP01' and comparisons with the parent and most similar variety of common knowledge are provided below.

General plant description:

*Plant habit.*—Perennial evergreen sedge; rhizomatous plant forming a dense clump of foliage.

*Height.*—60 cm as measured.

*Width.*—40 cm as measured.

*Propagation.*—Propagation is accomplished by dividing the crown of the plant and also by way of meristematic tissue culture propagation.

*Crop time.*—Time to initiate rooting is approximately 4 weeks; time to develop a rooted cutting is approximately 10 to 12 weeks. An average crop time is approximately 6 to 9 months to produce a mature and marketable 1-gallon nursery container, beginning with a rooted cutting.

*Environmental tolerances.*—Evergreen in USDA Hardiness Zones 8 through 11; adapt to temperatures ranging from approximately 25 degrees Fahrenheit to 110 degrees Fahrenheit. Shade and drought tolerant once established.

*Pest and disease susceptibility or resistance.*—Neither resistance nor tolerance to pests and diseases known to effect *Lepidosperma gladiatum* have been observed.

Roots: Densely rooting; comprised of rhizomes and fibrous roots; distributed evenly throughout the soil profile, from shallow to deep. Juvenile roots are yellow-white, RHS 158B, and mature roots are greyed-yellow, RHS 161C.

Culms:

*Culm attitude.*—Upright.

*Culm aspect.*—Flattened.

*Culm length.*—Approximately 1 cm.

*Color.*—Yellow-white, nearest to RHS 158C.

Foliage:

*Attachment.*—Basal.

*Division.*—Simple.

*Arrangement.*—Equitant.

*Shape.*—Linear; grass-like.

*Mature leaf dimensions.*—1.0 cm wide and 60 cm long, on average.

*Aspect.*—Flattened.

*Attitude.*—Erect to slightly arching.

*Apex.*—Acute.

*Base.*—Sheathed.

*Sheath color.*—Brown, nearest to RHS 200A, at the base and becoming greyed-orange towards the distal end, nearest to a combination of RHS 166A and 166B.

*Margins.*—Knife-like.

*Texture, adaxial surface.*—Glabrous; smooth.

*Texture, abaxial surface.*—Glabrous; smooth.

*Juvenile foliage color, adaxial surface.*—Yellow-green, RHS 144A.

*Juvenile foliage color, abaxial surface.*—Yellow-green, RHS 144A.

*Mature foliage color, adaxial surface.*—Yellow-green, RHS 144A.

*Mature foliage color, abaxial surface.*—Yellow-green, RHS 144A.

*Venation.*—Parallel.

*Vein color, adaxial surfaces.*—Indistinguishable from surrounding foliage, RHS 144A.

*Vein color, abaxial surfaces.*—Indistinguishable from surrounding foliage, RHS 144A.

Inflorescence:

*Type.*—Paniculate.

*Natural flowering season.*—Spring to early summer in Clarendon, NSW, Australia.

*Overall dimensions.*—Up to 125 mm long, excluding the peduncle, and 25 mm in diameter.

*Position of inflorescence relative to foliage.*—At or above the foliage.

*Bloom habit.*—Very floriferous.

*Spikelets.*—Dimensions — Approximately 10 mm long and 2 mm in diameter. General shape — Ovate outline with an acute apex. Quantity of spikelets per inflorescence — Varying from 70 to 90. Glumes — Approximately 5 to 7 glumes are present, spirally arranged; the lower 3 or 4 glumes are infertile; infertile glumes are approximately 3 to 4 mm long and fertile glumes are 4 to 5 mm long; apex is bluntly acute; the texture is puberulous; the color with pubescence removed is a combination of brown, RHS 200B, and greyed-orange, RHS 166A.

*Peduncle.*—Dimensions — Up to 360 mm long and 2 mm in diameter. Attitude — Erect to semi erect. Strength — Medium. Texture — Smooth. Color — Yellow-green, nearest to RHS 144A.

Reproduction organs: Not observed.

Seed: Not observed.

COMPARISONS WITH THE PARENT PLANT

Plants of the new cultivar 'LEP01' exhibit a short plant height of approximately 60 cm, whereas the seed parent, an unnamed *Lepidosperma gladiatum* plant, grows to approximately 100 cm tall. 'LEP01' has a narrow leaf of approximately 1 cm in width, whereas the seed parent has a wider leaf of approximately 1.5 cm in width.

COMPARISONS WITH THE MOST SIMILAR VARIETY OF COMMON KNOWLEDGE

Plants of the new cultivar 'LEP01' can be compared to the commercial cultivar, *Lepidosperma* sp. 'LEP01' (not patented), in that both are smaller than the species with a fine leaf texture. However, 'LEP01' exhibits light green foliage whereas the foliage of 'LEP08' is darker green. The foliage of 'LEP01' is broader than that of 'LEP08'. The inflorescence of 'LEP01' is positioned at or above the foliage, whereas the inflorescence of 'LEP08' is positioned within the foliage.

That which is claimed is:

1. A new and distinct variety of *Lepidosperma gladiatum* named 'LEP01', substantially as described and illustrated herein.

* * * * *